United States Patent
Linder et al.

(10) Patent No.: US 8,364,259 B2
(45) Date of Patent: Jan. 29, 2013

(54) HIGH VOLTAGE CAPACITOR ROUTE WITH INTEGRATED FAILURE POINT

(75) Inventors: William J. Linder, Golden Valley, MN (US); Ron A. Balczewski, Bloomington, MN (US); Jacob M. Ludwig, Isanti, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 102 days.

(21) Appl. No.: 12/952,554

(22) Filed: Nov. 23, 2010

(65) Prior Publication Data

US 2011/0066199 A1    Mar. 17, 2011

Related U.S. Application Data

(62) Division of application No. 11/677,793, filed on Feb. 22, 2007, now Pat. No. 7,856,265.

(51) Int. Cl.
*A61N 1/39* (2006.01)

(52) U.S. Cl. ............................................................ 607/5

(58) Field of Classification Search .................... 607/5–8
See application file for complete search history.

(56) References Cited

U.S. PATENT DOCUMENTS

| | | | |
|---|---|---|---|
| 3,025,441 A | 3/1962 | West | |
| 3,331,759 A | 7/1967 | Middelhoek | |
| 3,445,731 A | 5/1969 | Saeki et al. | |
| 3,627,520 A | 12/1971 | Rogers | |
| 3,644,796 A | 2/1972 | Carino | |
| 3,647,415 A | 3/1972 | Yano et al. | |
| 3,789,502 A | 2/1974 | Callins et al. | |
| 4,059,116 A | 11/1977 | Adams | |
| 4,085,397 A * | 4/1978 | Yagher, Jr. | 337/407 |
| 4,406,286 A | 9/1983 | Stein | |
| 4,442,473 A | 4/1984 | Holtzman et al. | |
| 4,687,951 A | 8/1987 | McElroy | |
| 4,840,122 A | 6/1989 | Nerheim | |
| 4,894,746 A | 1/1990 | Mori et al. | |
| 5,062,025 A | 10/1991 | Verhoeven et al. | |
| RE34,879 E | 3/1995 | Bocchi et al. | |
| 5,468,254 A | 11/1995 | Hahn et al. | |
| 5,591,211 A | 1/1997 | Meltzer | |
| 5,591,217 A | 1/1997 | Barreras | |
| 5,634,938 A | 6/1997 | Swanson et al. | |
| 5,807,397 A | 9/1998 | Barreras | |
| 5,874,770 A | 2/1999 | Saia et al. | |
| 5,930,109 A | 7/1999 | Fishler | |

(Continued)

FOREIGN PATENT DOCUMENTS

EP    1470267 B1    4/2009

OTHER PUBLICATIONS

"U.S. Appl. No. 11/677,793, Final Office Action mailed May 19, 2010", 5 pgs.

(Continued)

*Primary Examiner* — Eric D. Bertram

(74) *Attorney, Agent, or Firm* — Schwegman Lundberg & Woessner, P.A.

(57) ABSTRACT

An implantable medical device may have a circuit failure mode. The disclosed circuit may have an integrated failure point designed to fail prior to those portions of the circuit. The integrated failure point may include a narrowed portion of a high voltage lead and a grounded lead having a narrow gap separating the grounded lead from the narrowed portion of the high voltage lead. During a high stress fault condition the narrowed portion of the high voltage lead acts as a fuse, forming a vaporized cloud of metal, which shorts current in the high voltage lead across the narrow gap to the grounded lead, thus protecting the remaining portion of the circuit from the high stress condition.

22 Claims, 3 Drawing Sheets

U.S. PATENT DOCUMENTS

| | | | |
|---|---|---|---|
| 6,115,235 | A | 9/2000 | Naito |
| 6,161,040 | A * | 12/2000 | Blunsden .......................... 607/5 |
| 6,193,779 | B1 | 2/2001 | Reichert et al. |
| 6,241,751 | B1 | 6/2001 | Morgan et al. |
| 6,310,757 | B1 | 10/2001 | Tuzuki et al. |
| 6,347,032 | B2 | 2/2002 | Naito |
| 6,350,406 | B1 | 2/2002 | Satou et al. |
| 6,385,031 | B1 | 5/2002 | Lerche et al. |
| 6,456,877 | B1 | 9/2002 | Fishler |
| 6,699,265 | B1 | 3/2004 | O'Phelan et al. |
| 6,778,860 | B2 | 8/2004 | Ostroff et al. |
| 6,785,123 | B2 | 8/2004 | Keser |
| 6,801,424 | B1 | 10/2004 | Nielsen et al. |
| 6,807,048 | B1 | 10/2004 | Nielsen et al. |
| 6,850,405 | B1 | 2/2005 | Mileham et al. |
| 6,855,234 | B2 | 2/2005 | D'Astolfo, Jr. |
| 6,865,417 | B2 | 3/2005 | Rissmann et al. |
| 6,952,608 | B2 | 10/2005 | Ostroff |
| 6,954,670 | B2 | 10/2005 | Ostroff |
| 7,024,246 | B2 | 4/2006 | Acosta et al. |
| 7,327,557 | B2 | 2/2008 | Poplett |
| 7,522,957 | B2 | 4/2009 | Ostroff |
| 7,760,488 | B2 | 7/2010 | Breznova et al. |
| 7,856,265 | B2 | 12/2010 | Linder et al. |
| 2006/0035152 | A1 | 2/2006 | Nishimura et al. |
| 2007/0109727 | A1 | 5/2007 | Edson et al. |
| 2008/0198534 | A1 | 8/2008 | Lee et al. |
| 2008/0208270 | A1 | 8/2008 | Linder et al. |
| 2009/0231782 | A1 | 9/2009 | Fujita et al. |
| 2009/0237862 | A1 | 9/2009 | Nielsen et al. |
| 2009/0242415 | A1 | 10/2009 | Yoshimitsu |
| 2009/0273884 | A1 | 11/2009 | Shimizu et al. |
| 2010/0110614 | A1 | 5/2010 | Umemoto et al. |
| 2010/0110615 | A1 | 5/2010 | Nishimura et al. |
| 2010/0157510 | A1 | 6/2010 | Miyachi et al. |
| 2010/0193731 | A1 | 8/2010 | Lee et al. |
| 2010/0195261 | A1 | 8/2010 | Sweeney et al. |
| 2010/0226066 | A1 | 9/2010 | Sweeney et al. |
| 2010/0226070 | A1 | 9/2010 | Yang et al. |
| 2011/0317370 | A1 | 12/2011 | Sherwood |

OTHER PUBLICATIONS

"U.S. Appl. No. 11/677,793, Non-Final Office Action mailed Sep. 29, 2009", 12 pgs.

"U.S. Appl. No. 11/677,793, Notice of Allowance mailed Aug. 11, 2010", 8 pgs.

"U.S. Appl. No. 11/677,793, Response filed Jan. 28, 2010 to Non Final Office Action mailed Sep. 29, 2009", 16 pgs.

"U.S. Appl. No. 11/677,793, Response filed Jul. 19, 2010 to Final Office Action mailed May 19, 2010", 10 pgs.

Bocek, Joseph M, et al., "Method and Apparatus for Charging Partitioned Capacitors", U.S. Appl. No. 11/462,301, filed Aug. 3, 2006, 53 pgs.

"U.S. Appl. No. 11/677,793, Response filed Jun. 15, 2009 to Restriction Requirement mailed May 13, 2009", 10 pgs.

"U.S. Appl. No. 11/677,793, Restriction Requirement mailed May 13, 2009", 10 pgs.

\* cited by examiner

HIGH VOLTAGE CAPACITOR ROUTE WITH INTEGRATED FAILURE POINT

CROSS-REFERENCE TO RELATED APPLICATIONS

This application is a Division of U.S. application Ser. No. 11/677,793, filed on Feb. 22, 2007, now issued as U.S. Pat. No. 7,856,265, the benefit of priority of which is claimed herein, and which is incorporated herein by reference in its entirety.

TECHNICAL FIELD

This disclosure relates generally to fabrication of an integrated failure point in a circuit design to protect the remainder of the circuit from damage, and to device electrical overstress protection methods, and to implantable medical devices.

BACKGROUND

As implantable medical devices continue to decrease in size, the circuit and component layouts enclosed within the device will generally increase in density. This increase in device density may result in device spacing and circuit metal line spacing that may be very close, and may result in cross talk or even arcing. This may be an issue, particularly in an electronic device using high voltage levels.

OVERVIEW

The present inventors have recognized that, in the case of implantable cardioverter defibrillators (ICDs) and cardiac resynchronization therapy defibrillators (CRT-Ds), close circuit trace spacing may lead to a situation where an electrical overstress on one circuit may damage adjacent circuits. This is because the electrical overstress may cause intense local heating, and circuit burnout that can overheat or short to adjacent circuits.

Electronic devices may use fuses to burn out and open up a metal trace that is carrying more power than the downstream components can withstand. A potential issue with the use of fuse, however, is that the time during which the fuse is burning out may result in significant damage to the remainder of the circuit downstream from the fuse. Essentially, the fuse does not burnout fast enough to fully protect the rest of the circuit.

Thus, there is a need for improved structures and methods with respect to the manufacture of implantable medical devices. In particular, there is a need for a power disconnect method that is faster than a fuse.

DETAILED DESCRIPTION

Figure 1:
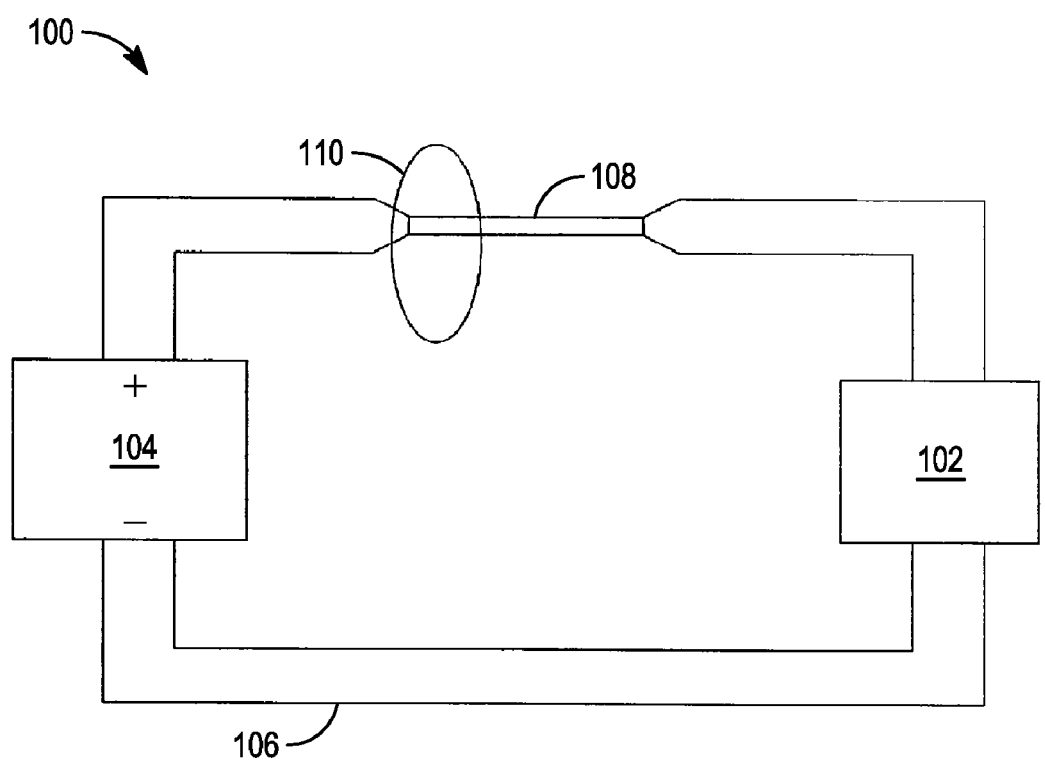
FIG. 1 illustrates an example of a circuit.

In any electronic device, and especially implantable medical devices, there is a need to disconnect circuit elements and conductive lines from a failed portion of the circuit, to prevent further circuit damage. A simple fuse may serve the function of disconnecting the circuit from an overstress situation, but may not burn out fast enough to prevent downstream damage. This may be true for various reasons, including not providing the fuse with sufficient resistance to rapidly heat during an overstress situation, or it may be due to evaporation of the fuse material during burn out forming a conductive plasma around the burn out site. This arcing may result in the fuse remaining in a conductive state for a short period after the evaporation of the fuse, at least until the evaporated fuse material disperses enough to prevent the arcing over the fuse gap. Thus, the gap formed by the rapid heating of the resistive fuse element may not be enough to fully protect the rest of the circuit, or the patient. One way to increase the rate of disconnecting a circuit from an overstress situation, either high voltage, high current or high power, is to add a switch responsive to the overstress situation, wherein the switch at least temporarily connects the overstress to a sink, or a ground, or negative pole of a capacitor.

Another way to improve the disconnect rate would include building intentional failure points into the circuit, for example, at locations that have lower resistive paths to a ground supply. Integrating these failure points into the circuit design may increase the ability of the device to rapidly and reliably disconnect the circuit from any overstress surges, particularly in view of the repeatability and precision of integrated manufacturing operations, such as PCB and IC manufacturing. In an illustrative example, an integrated failure point may include a fuse formed by narrowing a conductive trace to increase the resistance to a level that will burn out by evaporation of the conductive trace material at an overstress level that is below a value likely to cause damage to the remainder of the circuit or the patient. A second conductive trace, connected to a ground voltage source by a low resistance connection, may dead-end in close proximity the fuse, such as near the high voltage end of the fuse. In certain examples, the second conductive trace is separated from the fuse by a spacing that is equal to the design rule specifying the minimum metal-to-metal spacing of the circuit technology being used to fabricate the circuit. For example, a standard PCB manufacturing process may have copper and solder conductive traces. A minimum spacing design rule may specify that such traces must be separated from each other by about 0.010 inches. During an overstress situation, the fuse may begin to overheat and vaporize, thereby forming a gap having a length that is larger than the minimum design rule spacing. Thus, the dead-end of the second conductive trace may now be closer to the high voltage end of the fuse than the other side of the burned-out gap in the fuse. In addition, since the second conductive trace is directly connected to ground, the current path through the second conductive trace has a lower resistance compared to the current path across the fuse gap and through the remainder of the circuit. In this situation, the vaporized fuse material may form a temporary conductive arc between the high voltage end of the fuse and the second conductive trace. This will rapidly reduce the current flowing to the remainder of the circuit. The vaporized fuse material supporting the temporary arc forms a conductive gas, which may be called a plasma, and the described arrangement may be called a plasma switch.

It should be noted that the described illustrative examples are not intended to be limited to the disclosed arrangements and methods, but may include any method of forming a circuit, fuse and switch. For example, the structure may be formed of any combination of metals, PCBs, hybrids or semiconductors, having insulator oxides, nitrides, polymers or combinations thereof. In another example, the structure may be formed using the circuit and fuse with no switch where the fuse has been positioned to minimize damage to adjacent circuits.

FIG. 1 illustrates one example of a circuit for protecting against overstress situations. The device 100, which may comprise a hybrid circuit, devices on a PCB, or a monolithic IC, has a circuit 102 to be protected from an overstress generated by a failure or power spike in a power source 104, such as a high voltage capacitor. The circuit 102 and the power source 104 are connected by conductive traces 106, and a fuse 108. The fuse 108 may have a higher resistance that the conductive traces 106, and be formed of a different material, or be formed of the same material but having a smaller current carrying cross section. One method of reducing the current carrying cross section is to reduce the conductive trace width to the minimum design rule for the technology. The fuse 108 will evaporate under the heating effects of an overstress situation, for example at the location 110, which may be at the connection point between the fuse 108 and the conductive trace 106 closest to the power source 104. The evaporation of the fuse at location 110 creates a gap in the fuse 108, but during the evaporation process, the gaseous fuse material may form a plasma in the region 110 and temporarily continue to conduct current and voltage across the gap in fuse 108. The addition of a switch connecting the region 110 to the negative portion of the power source 104 could be implemented to provide a lower resistance than the path through the conductive traces 106 to the functional circuit 102 and back to the power source 102. In such a scenario, the switch would essentially short circuit the functional circuit 102, and take it out of the power circuit, thus providing improved protection. The present inventors have recognized that a plasma switch is inexpensive to form, and may provide a reliable and reproducible failure point that may be integrated into the circuit, such as during a standard circuit manufacturing process.

Figure 2:
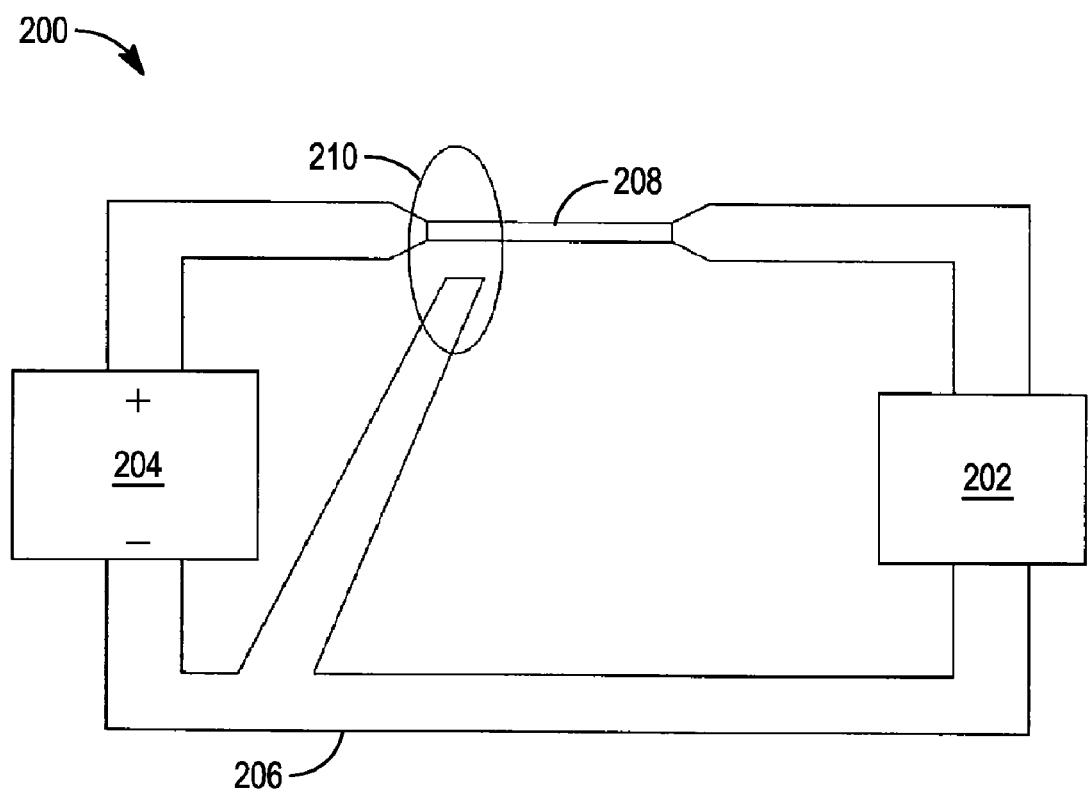
FIG. 2 illustrates an integrated protection circuit according to various examples.

FIG. 2 illustrates an example of an integrated protection circuit 200 that includes a plasma switch formed by the addition of the conductive trace 212 to the circuit of FIG. 1. In this arrangement the evaporation of the fuse material in the region 210 allows any potential arcing to jump to the lower resistance path formed by the proximity of the conductive trace 212 and the lower resistance path formed by traces 212 and 206, as compared to the longer path through the functional circuit 202. Such plasma switches may be particularly useful in high voltage or other medical devices, integrated circuits, and other electronic devices. In an example, the conductive traces 212 and 206 are both formed in a single metal trace layer of a multilayer PCB, and are thus formed of the same material having the same thickness and insulation properties. In such an example, the trace 212 will be separated from the fuse 208 by at least distance that is equivalent to the minimum design rule spacing between such same-layer conductive traces. The overstress level that is capable of forming the plasma switch depends upon design factors including the material used and the spacing. In certain examples, smaller spacing (and consequent lower voltage plasma switch operation levels) may be obtained by using different conductor levels for traces 212 and 206, and using the layer-to-layer alignment accuracy of the manufacturing process to determine the gap, particularly useful if such accuracy is reproducible in a manufacturing setting. In certain examples, the region over at least a portion of the fuse 208 and the tip of the trace 212 may have an overlying insulator layer removed, such as to increase the rate at which the plasma switch forms, particularly useful if long term corrosion resistance of the fuse is not compromised.

Figure 3:
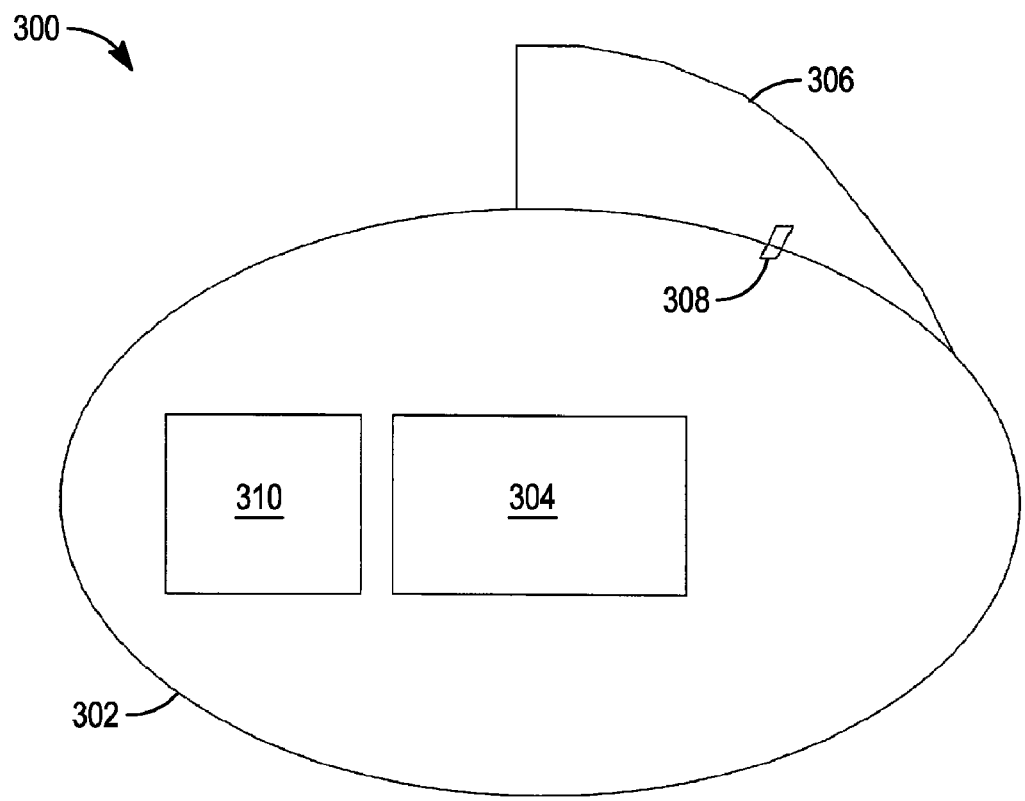
FIG. 3 illustrates an implantable device in accordance with various examples.

FIG. 3 illustrates an implantable device 300, such as a defibrillator or other cardiac function management device, placed within the body of a patient. The defibrillator circuit may be contained within a hermetic housing body 302, which may be formed of a biocompatible material. The functional circuit 304 may contain the measurement and evaluation circuits to determine if the patient requires shock therapy, which may be delivered to the heart of the patient by electrodes, which may be located on one or more therapeutic leads traveling out of the pulse generator body 302 through the header 306 via one or more hermetic pass through 308. The circuit 304 may connect a power source 310, for example a high voltage capacitor, to the heart for shock therapy, such as pace making or cardioverting. A plasma switch located between the power source 310 and the functional circuit 304 may be used to disconnect the power source 310 from the functional circuit 304 in the case of an electrical overstress situation, which may otherwise cause an undesirable high voltage current to pass into the patient's heart or cause damage to unrelated portions of the device that might otherwise still provide therapy or failure enunciation.

It should be understood that some examples are equally applicable to any size and type of circuit and are not intended to be limited to a particular type of device, such as the illustrative implantable cardiac function management device. For example, the described examples may be formed on an integrated circuit (IC), on a thick film hybrid circuit board, or on a printed circuit board (PCB), each with different minimum design rule line width and spacing for the fuses, switches and devices. Another example may be to position the fuse internal to the power source 310 or in the header 306.

Some examples may include an implantable medical device including a voltage source having first and second terminals, and a functional circuit, also having first and second terminals coupled to the first and second terminals of the voltage source, for example power and ground terminals. There may be a fuse coupled between one of the first and second terminals of the voltage source and one of the first and second terminals of the functional circuit to protect the functional circuit from electrical overstress situations, and thus protect a patient from inadvertent harm. The fuse may be located either inside or outside of the voltage source, and may be coupled in series with the first and second terminals. The fuse alone may not interrupt the electrical overstress immediately due to vaporized portions of the fuse material continuing to conduct high voltage or current flows across the burned fuse for a short time period. To address this issue there may be a plasma switch, adapted such that when power in the fuse exceeds a selected fault power threshold, causes an arcing current to be conducted from the fuse to a node at the other one of the first and second terminals of the voltage source such that the current is directed away from the functional circuit. The plasma switch essentially forms an immediate shunt to direct power away from the functional circuit.

The plasma switch may include a shunting conductor with a first terminal located at a specified distance away from the fuse, or at a specified distance away from a conductor to or from the fuse, and the conductor may include a second terminal coupled to the other one of the first and second terminals of the voltage source, for example power and ground. The plasma switch at the specified distance from the fuse or the conductor near the fuse may establish the arcing current to shunt the power away from the functional circuit when the fault power threshold is exceeded. The specified distance between the shunting conductor and the fuse may typically be substantially equal to the minimum design rule distance between unrelated conductors of the printed circuit board that includes the plasma switch and functional circuit, in order to create the plasma switch arc at the lowest possible voltage level, unless the maximum desired voltage level is higher than the lowest obtainable level, in which case the spacing between the plasma switch conductor and the fuse will be increased to obtain the desired voltage level for the plasma switch operation. The fuse and plasma switch may both be a portion of a single wiring layer of the printed circuit board so that the insulation between wiring layers does not interfere in the arc voltage point, and the printed circuit board may include a hole in the board insulation or dielectric in a region near the fuse and the plasma switch. The dielectric material may include polyimide, parylene or other organic insulative material. Selecting the fault power threshold to trigger the plasma switch may include determining a combination of features such as the wiring material, wiring thickness and width, the fuse width and ground conductor width for a wiring layer of the printed circuit. The wiring material may include copper, tin or solder.

The apparatus may comprise a first conductor having a first resistance per unit length connecting the first terminal to a resistive circuit element having a resistance per unit length greater than the resistance per unit length of the first conductor, so that the resistive element is the fuse. A second conductor may connect the resistive circuit element to the first terminal of the functional circuit, and a third conductor may connect the second terminal of the functional circuit to the second terminal of the voltage source, thus completing the normal functional circuit power and ground connections. A fourth conductor may connect the second terminal of the voltage source, for example the ground terminal, to within a predetermined distance of the resistive circuit element, such as a specified minimum design rule spacing. Illustrative example spacing for a printed circuit board may be about 0.010 inches, with smaller possible spacing for hybrid circuits and for integrated circuits (ICs). This may allow the arcing current to flow between the resistive element and the fourth conductor when the fault power threshold is exceeded. The fourth conductor may thus provide an electrical shunting conductor to pull power away from the functional circuit while the fuse burns completely open, and thus improve protection of the functional circuit over a simple fuse itself.

Another example may include a method for forming an implantable medical device circuit on a printed wiring board, a hybrid circuit board, or on an integrated circuit device. The method may include forming a fuse between a power source and the medical device circuit and forming a plasma switch between the fuse and a ground source. The plasma switch may disconnect the power source from the medical device circuit and at least temporarily connect the power source to the ground source in response to an electrical overstress condition. Forming the plasma switch may include locating a portion of an electrical conductor that is directly connected to the ground source, close to a portion of the fuse, or a portion of an electrical conductor between the power source and the fuse. The separation distance is generally selected to form an arc when the power source exceeds a threshold value. The arc provides a low resistance path to ground during the fuse burnout, thus reducing or eliminating the current flow to the medical device circuit more quickly than with a fuse alone. Triggering the plasma switch may include selecting a combination of the distance between the electrical conductor connected to the ground source and the portion of the fuse, the fuse material, thickness, length, and width of the fuse, which partially control the fuse resistance, and a power source voltage level which represents the electrical overstress condition. Forming the fuse may further include selecting the fuse properties to cause the fuse to vaporize into a cloud of ions when the electrical overstress condition occurs. The cloud of ions form a temporary arc between the fuse and the nearby ground conductor to shunt the electrical overstress to ground and away from the remainder of the circuit. In an example, the distance between the electrical conductor connected to the ground source and the fuse is selected to be substantially equal to the minimum design rule spacing for two unconnected metal features on the printed circuit board, hybrid circuit, or integrated circuit containing the plasma switch.

Another example may include a method for forming an implantable medical device circuit on a printed wiring board, a hybrid circuit board, or on an integrated circuit device. The method may include forming a fuse between a power source and the medical device circuit and forming a plasma switch between the fuse and a ground source. The plasma switch may disconnect the power source from the medical device circuit and at least temporarily connect the power source to the ground source in response to an electrical overstress condition. Forming the plasma switch may include locating a portion of an electrical conductor that is directly connected to the ground source, close to a portion of the fuse, or a portion of an electrical conductor between the power source and the fuse. The separation distance is generally selected to form an arc when the power source exceeds a threshold value. The arc provides a low resistance path to ground during the fuse burnout, thus reducing or eliminating the current flow to the medical device circuit more quickly than with a fuse alone. Triggering the plasma switch may include selecting a combination of the distance between the electrical conductor connected to the ground source and the portion of the fuse, the fuse material, thickness, length, and width of the fuse, which partially control the fuse resistance, and a power source voltage level which represents the electrical overstress condition. Forming the fuse may further include selecting the fuse properties to cause the fuse to vaporize into a cloud of ions when the electrical overstress condition occurs. The cloud of ions form a temporary arc between the fuse and the nearby ground conductor to shunt the electrical overstress to ground and away form the remainder of the circuit. In an example, the distance between the electrical conductor connected to the ground source and the fuse is selected to be substantially equal to the minimum design rule spacing for two unconnected metal features on the printed circuit board, hybrid circuit, or integrated circuit containing the plasma switch.

In another example, a method for delivering defibrillation shock energy from an implantable shock therapy energy storage capacitor to a subject through a functional circuit may include detecting an electrical overstress condition, and shunting the defibrillation shock energy from the capacitor away from the functional circuit and to a circuit power or ground node in response to detecting the electrical overstress condition. The shunting may be provided by a switch, a plurality of resistors in a network, a fuse, a transistor, a Hall effect switch, a magnetic switch, a microswitch, a solenoid, or a plasma switch. Shunting may open the electrical connection to the functional circuit, and close a temporary electrical connection to the ground node, thus protecting a patient from the overstress.

Detecting the electrical overstress condition may be by selecting a fuse material, a fuse material vaporization temperature, a fuse cross sectional area, a fuse length, a overlaying insulation material, and a fuse resistance to cause the fuse to heat to the vaporization temperature at the electrical overstress condition. The fuse may then vaporize and form an open conductor to the functional circuit, thus preventing the circuit from being damaged by the overstress. Forming an electrical gap between the fuse material and the electrical connection to the ground node, where the gap is designed to have a dimension selected to be within a cloud of vaporized fuse material caused by the electrical overstress condition, may improve the disconnection speed. The cloud may more easily form an electrical conduction path to the ground node, thus shunting current away from the functional circuit while the fuse is still burning open.

Another example may include an implantable defibrillator having an implantable bio-compatible hermetic casing, such as the pulse generators cases which may be used in cardiac pacemakers. Within the casing there may be a defibrillation circuit including one or more shock therapy energy storage capacitors. There may be at least one fuse located between the storage capacitor and the defibrillation circuit, where the fuse may interrupt electrical power to the defibrillation circuit in the case of an overstress condition. The casing may further include a pacemaker, an acoustic sensor, an RF generator, an antenna and a circuit for generating and receiving RF signals from internal and external devices, a cardiac resynchronizer, or a cardioverter. The implantable defibrillator may further include an electrical shunt switch connecting the fuse to a ground connection. The electrical shunt switch may be a plasma switch, a mechanical switch, an electronic switch or a magnetic switch.

An example of a method of protecting a circuit from electrical overstress may include forming one or more fuses between a power supply and the circuit to be protected, or in series connection with the terminals of the power supply, either inside or outside of the power supply. There may be one or more grounded conductor lines located a short selected distance away from each of the fuses to form integrated failure points between the power supply and the circuit. The failure level may be selected by choosing the fuse material, thickness, width, length and resistance to vaporize the fuse material when the power level reaches above a set point. The distance between one of the fuses and a grounded conductor may be smaller than one of the other distances between a second fuse and a second grounded conductor to provide a series of failure points that may be used to dissipate the stored energy in a distributed fashion. The functional circuit to be protected may be part of a printed circuit board (PCB), and the resistors, fuses and switches may be formed of the multiple conductor layers found in multilayer PCBs, including copper traces and solder conductors. The resistive element may be a fuse, and the fuse may include an opening in any overlaying insulator material to assist in adjusting the overstress level that will cause a blow out. In an example the fuse and the grounded conductor may form a plasma switch that may rapidly temporarily connect the blowing fuse to the negative power terminal and to thus electrically disconnect the remaining portion of the circuit from the positive terminal during the period in which the fuse has vaporized, but the metallic vapor is still able to conduct electrical overstress power to the circuit. Thus, the plasma switch improves the rate at which the fuse blowout disconnects the electrical overstress from the circuit to be protected. The resistive element, fuse and a plasma switch may all be formed in the same single wiring layer in a printed circuit board.

An example of a method of using an implantable medical device includes determining the condition of a patient with an implantable medical device implanted, evaluating whether to initiate a course of shock therapy, and delivering energy from an energy storage capacitor to the patient through a circuit. While the shock is occurring detecting any possible harmful electrical overstress condition in the shock therapy energy, either harmful to the circuit or to the patient, and shunting the energy away from the functional circuit and the patient, to an energy sink. There are several methods to perform the shunting, including shunting the shock energy to the energy sink using a ground electrical connection, either by burning out a fuse between the shock capacitor and the circuit, or by adding an electrical switch between the end of the fuse located nearest the shock therapy energy storage capacitor and the ground electrical connection. The switch may be a plasma switch because plasma switches may most rapidly divert energy away from the fuse being burned out and thus prevent more of the capacitor overstress from reaching the circuit or the patient.

The detailed description refers to the accompanying drawings that show, by way of illustration, specific aspects and examples in which the present disclosed examples may be practiced. These examples are described in sufficient detail to enable those skilled in the art to practice aspects of the present invention. Other examples may be utilized, and structural, logical, and electrical changes may be made without departing from the scope of the disclosed examples. The various examples are not necessarily mutually exclusive, as some examples can be combined with one or more other examples to form new examples.

Although specific examples have been illustrated and described herein, it will be appreciated by those of ordinary skill in the art that any arrangement that is calculated to achieve the same purpose may be substituted for the specific examples shown. This application is intended to cover any adaptations or variations of examples of the present invention. It is to be understood that the above description is intended to be illustrative, and not restrictive, and that the phraseology or terminology employed herein is for the purpose of description and not of limitation. Combinations of the above examples and other examples will be apparent to those of skill in the art upon studying the above description. The scope of the present disclosed examples includes any other applications in which examples of the above structures and fabrication methods are used. The detailed description is, therefore, not to be taken in a limiting sense, and the scope of the present invention is defined only by the appended claims, along with the full scope of equivalents to which such claims are entitled.

What is claimed is:

1. A method, comprising:
   delivering defibrillation shock energy from an implantable shock therapy energy storage capacitor to a subject through an electrical circuit disposed on at least one of printed wiring board, a hybrid circuit board, or an integrated circuit device;
   in response to the delivered defibrillation shock energy exceeding a threshold, triggering a plasma switch to switch into shunting the defibrillation shock energy being delivered from the capacitor away from the electrical circuit and to at least one of a circuit power or ground node, including vaporizing material to form a cloud of vaporized material to form an electrical conduction path from the electrical circuit to the node, wherein the cloud is to bridge a nonconductive gap between the electrical circuit and the node, the gap having a dimension selected to be within the cloud of vaporized material.

2. The method of claim 1, wherein shunting the capacitor shock therapy energy away from the electrical circuit includes using at least one of a plurality of resistors, a fuse, a transistor, a Hall effect switch, a magnetic switch, a microswitch or a solenoid to open an electrical connection to the electrical circuit and close an electrical connection to the node.

3. The method of claim 2, wherein the material comprises the fuse.

4. The method of claim 3, wherein the fuse forms is disposed between the capacitor and the electrical circuit and is selected to heat to a vaporization temperature at the threshold.

5. The method of claim 1, comprising shunting the capacitor shock therapy energy away from the electrical circuit using the plasma switch to open an electrical connection to the electrical circuit and close an electrical connection to the ground node.

6. The method of claim 1, further comprising selecting the threshold by selecting a fuse material, a fuse material vaporization temperature, a fuse cross sectional area, a fuse length, and a fuse resistance to cause a fuse connected between the capacitor and the electrical circuit to heat to the fuse vaporization temperature at the threshold, to vaporize the fuse and form an open conductor to the electrical circuit.

7. The method of claim 6, further comprising forming a nonconductive gap between the fuse material and the electrical connection to the node, the gap having a dimension selected to be within a cloud of vaporized fuse material from the delivered defibrillation shock energy exceeding the threshold, and forming an electrical conduction path to the node with the cloud.

8. The method of claim 1, comprising detecting an electrical overstress condition in the electrical circuit and in response to detecting the electrical overstress condition, triggering the plasma switch.

9. A method of using an implantable medical device, comprising:
determining a present condition of a patient having an implantable medical device implanted within the patient;
evaluating the present condition and determining whether to initiate a course of shock therapy;
delivering defibrillation shock energy from an implantable shock therapy energy storage capacitor to a subject through an electrical circuit; and
in response to the delivered defibrillation shock energy exceeding a threshold, triggering a plasma switch to switch into shunting the defibrillation shock energy being delivered from the capacitor away from the electrical circuit and to a circuit power or ground node, wherein shunting the defibrillation shock energy includes forming the plasma switch from fuse vapor of a burned fuse in electrical communication with the capacitor.

10. The method of using of claim 9, comprising forming the plasma switch between an end of the fuse located nearest the shock therapy energy storage capacitor and the ground electrical connection.

11. The method of claim 9, wherein the fuse is disposed between the capacitor and the electrical circuit and the fuse vapor is to bridge a nonconductive gap between the fuse and the node, the gap having a dimension selected to be within the cloud of vaporized material.

12. A method, comprising:
forming an implantable medical device circuit, for providing a defibrillation shock energy, on at least one of a printed wiring board, a hybrid circuit board, or an integrated circuit device;
forming a fuse between a capacitor and the medical device circuit; and
forming a plasma switch between the fuse and a ground source;
wherein the plasma switch is for, in response to the defibrillation shock energy being delivered from implantable medical device circuit and exceeding a threshold, triggering a disconnecting of the capacitor from the medical device circuit and for triggering an at least temporary connecting of the capacitor to the ground source,
wherein the plasma switch is for shunting the defibrillation shock energy being delivered from the capacitor away from the electrical circuit and to a circuit power or ground node, wherein shunting the defibrillation shock energy includes forming the plasma switch from fuse vapor of a burned fuse in electrical communication with the capacitor.

13. The method of claim 12, wherein forming the plasma switch includes locating a portion of an electrical conductor connected to the ground source close to at least one of a portion of the fuse and a portion of a second electrical conductor connecting the capacitor and the fuse.

14. The method of claim 13, wherein forming the plasma switch includes locating a portion of the electrical conductor connected to the ground source close to the portion of the fuse.

15. The method of claim 13, wherein the fuse forms a part of the electrical circuit and comprising selecting at least one of a distance between the electrical conductor connected to the ground source and the portion of the fuse, a material of the fuse, a thickness of the fuse, a length of the fuse, a width of the fuse, a resistance of the fuse and a capacitor voltage level to select the threshold for triggering the plasma switch.

16. The method of claim 15, comprising selecting the distance between the electrical conductor connected to the ground source and the portion of the fuse to select the threshold.

17. The method of claim 15, comprising selecting a property of at least a portion of the fuse to vaporize as a cloud of ions in response to the delivered defibrillation shock energy exceeding a threshold.

18. The method of claim 17, comprising selecting the distance between the electrical conductor connected to the ground source and the fuse to be substantially equal to a minimum design rule space for two unconnected metal features on a printed circuit board, a hybrid and an integrated circuit.

19. The method of claim 12, wherein forming an implantable medical device circuit on at least one of a printed wiring board, a hybrid circuit board, and an integrated circuit device includes forming a hole in a dielectric of at least one of a printed wiring board, a hybrid circuit board, and an integrated circuit device, with the fuse disposed over the hole.

20. The method of claim 12, comprising forming the implantable medical device circuit on the printed wiring board.

21. A method, comprising:
delivering defibrillation shock energy from an implantable shock therapy energy storage capacitor to a subject through an electrical circuit;
in response to the delivered defibrillation shock energy exceeding a threshold, triggering a plasma switch to switch into shunting the defibrillation shock energy being delivered from the capacitor away from the electrical circuit and to a circuit power or ground node;
selecting the threshold by selecting a fuse material, a fuse material vaporization temperature, a fuse cross sectional area, a fuse length, and a fuse resistance to cause a fuse connected between the capacitor and the electrical circuit to heat to the fuse vaporization temperature at the threshold, to vaporize the fuse and form an open conductor to the electrical circuit; and forming a nonconductive gap between the fuse material and the electrical connection to the node, the gap having a dimension selected to be within a cloud of vaporized fuse material from the delivered defibrillation shock energy exceeding the threshold; and forming an electrical conduction path to the node with the cloud.

22. A method of using an implantable medical device, comprising:

determining a present condition of a patient having an implantable medical device implanted within the patient;

evaluating the present condition and determining whether to initiate a course of shock therapy;

delivering defibrillation shock energy from an implantable shock therapy energy storage capacitor to a subject through an electrical circuit; and in response to the delivered defibrillation shock energy exceeding a threshold, triggering a plasma switch to switch into shunting the defibrillation shock energy being delivered from the capacitor away from the electrical circuit and to a circuit power or ground node, wherein shunting the shock therapy energy to the energy sink includes shunting to the node, wherein shunting the shock therapy energy to the node includes burning out a fuse located between the shock therapy energy storage capacitor and the electrical circuit.

\* \* \* \* \*